United States Patent
Kajihara et al.

(10) Patent No.: US 8,694,264 B2
(45) Date of Patent: Apr. 8, 2014

(54) MASS SPECTROMETRY SYSTEM

(75) Inventors: Shigeki Kajihara, Kyoto (JP); Jingwen Yao, Manchester (GB); Matthew Kelly, Manchester (GB)

(73) Assignee: Shimadzu Corporation, Kyoto-Shi (JP)

( * ) Notice: Subject to any disclaimer, the term of this patent is extended or adjusted under 35 U.S.C. 154(b) by 835 days.

(21) Appl. No.: 12/808,747

(22) PCT Filed: Dec. 20, 2007

(86) PCT No.: PCT/JP2007/001439
§ 371 (c)(1),
(2), (4) Date: Aug. 10, 2010

(87) PCT Pub. No.: WO2009/081446
PCT Pub. Date: Jul. 2, 2009

(65) Prior Publication Data
US 2010/0299076 A1    Nov. 25, 2010

(51) Int. Cl.
*G06F 19/00* (2011.01)
*H01J 49/26* (2006.01)

(52) U.S. Cl.
USPC .......................................... 702/19; 422/68.1

(58) Field of Classification Search
CPC . G01N 33/00; G01N 33/48; G01N 2009/022; G01N 2015/0065; G01N 2030/009; G01N 21/00; G01N 2560/00; G01N 33/53; G01N 33/567; G06F 19/00; H01J 49/00; H01J 49/26; H01J 49/0027; H01J 49/004
USPC ...................................................... 702/27, 19
See application file for complete search history.

(56) References Cited

U.S. PATENT DOCUMENTS

| | | | | |
|---|---|---|---|---|
| 6,914,239 B2 * | 7/2005 | Yoshinari et al. | ............. | 250/281 |
| 6,917,037 B2 * | 7/2005 | Ootake et al. | ................. | 250/282 |
| 7,473,892 B2 * | 1/2009 | Sano et al. | .................... | 250/281 |

(Continued)

FOREIGN PATENT DOCUMENTS

| | | |
|---|---|---|
| JP | 2004-254699 | 9/2004 |
| JP | 2004-257922 | 9/2004 |
| JP | 2007-278712 | 10/2007 |

OTHER PUBLICATIONS

Translation of the International Preliminary Report on Patentability and Written Opinion of the International Authority.

*Primary Examiner* — John Breene
*Assistant Examiner* — Ruihua Zhang
(74) *Attorney, Agent, or Firm* — Bingham McCutchen LLP

(57) ABSTRACT

(EN) MS analysis, $MS^2$ analysis, ..., $MS^P$ analysis for peptide mixture are sequentially executed to obtain respective mass spectra (S1). At this time, an analysis in which precursor ion is changed or a different cleavage condition is set for the same precursor ion is performed plural times to put together peaks appearing in mass spectra that are obtained respectively. After the number of peaks is increased, a useful peak is extracted using commonality and complementarity of the peaks of $MS^m$ spectrum and $MS^{m+1}$ spectrum and classification is performed for each type of peaks extracted to obtain an appearance frequency for each classification (S3, S4). An evaluation score on whether the extracted peak is a product ion and on a terminal is calculated based on reliability and appearance frequency that are obtained in advance (S8). The evaluation score is used in estimating sequence with the use of the extracted peak to decide and output, for example, the priority of sequence candidates (S8, S9).

4 Claims, 3 Drawing Sheets

(56) References Cited

U.S. PATENT DOCUMENTS

| | | | |
|---|---|---|---|
| 2004/0169138 A1* | 9/2004 | Ootake et al. | 250/281 |
| 2004/0181347 A1* | 9/2004 | Yoshinari et al. | 702/27 |
| 2005/0063864 A1* | 3/2005 | Sano et al. | 422/68.1 |
| 2006/0043281 A1* | 3/2006 | Yoshinari et al. | 250/282 |
| 2007/0221836 A1* | 9/2007 | Kobayashi et al. | 250/282 |
| 2009/0166522 A1* | 7/2009 | Umemura | 250/281 |
| 2010/0312489 A1* | 12/2010 | Yamaguchi | 702/23 |

* cited by examiner

| # | b-H2O | b-NH3 | a | a-H2O | a-NH3 | b | Seq | y | y-H2O | y-NH3 | # |
|---|---|---|---|---|---|---|---|---|---|---|---|
| 1 | 129.1028 | | 101.1079 | | 84.0813 | 129.1293 | K | | | | 15 |
| 2 | 228.1712 | 211.1446 | 200.1763 | | 183.1497 | 245.1977 | V | | | | 14 |
| 3 | 325.224 | 308.1974 | 297.229 | | 280.2025 | 342.2505 | P | 1537.823 | 1511.843 | 1494.817 | 13 |
| 4 | 453.2825 | 436.256 | 425.2876 | | 406.2611 | 470.3091 | Q | 1438.754 | 1412.775 | 1395.748 | 12 |
| 5 | 552.3509 | 535.3244 | 524.356 | | 507.3295 | 569.3775 | V | 1341.701 | 1315.722 | 1298.696 | 11 |
| 6 | 639.383 | 622.3564 | 611.3881 | 593.3775 | 594.3615 | 656.4095 | S | 1213.643 | 1187.664 | 1170.637 | 10 |
| 7 | 740.4307 | 723.4041 | 712.4357 | 694.4252 | 695.4092 | 757.4572 | T | 1114.574 | 1088.595 | 1071.569 | 9 |
| 8 | 837.4834 | 820.4569 | 809.4885 | 791.4779 | 792.4619 | 854.51 | P | 1027.542 | 1001.563 | 984.5366 | 8 |
| 9 | 938.5311 | 921.5045 | 910.5362 | 892.5256 | 893.5096 | 955.5576 | T | 926.4947 | 900.5154 | 883.4889 | 7 |
| 10 | 1051.615 | 1034.589 | 1023.62 | 1005.61 | 1006.594 | 1068.642 | L | 829.4419 | 803.4627 | 786.4361 | 6 |
| 11 | 1150.684 | 1133.657 | 1122.689 | 1104.678 | 1105.662 | 1167.71 | V | 728.3943 | 702.415 | 685.3885 | 5 |
| 12 | 1279.726 | 1262.7 | 1251.731 | 1233.721 | 1234.705 | 1296.753 | E | 615.3102 | 589.3309 | 572.3044 | 4 |
| 13 | 1378.795 | 1361.768 | 1350.8 | 1332.789 | 1333.773 | 1395.821 | V | 516.2418 | 490.2625 | 473.236 | 3 |
| 14 | 1465.827 | 1448.8 | 1437.832 | 1419.821 | 1420.805 | 1482.853 | S | 387.1992 | 361.2199 | 344.1934 | 2 |
| 15 | | | | | | | R | 288.1308 | 262.1515 | 245.125 | |
| | | | | | | | | 201.0988 | 175.1195 | 158.093 | 1 |

MS3(y13) : PC$_{MS3}$=1412.775

| # | b-H2O | b-NH3 | a | a-H2O | a-NH3 | b | Seq | y | y-H2O | y-NH3 | # |
|---|---|---|---|---|---|---|---|---|---|---|---|
| 1 | 98.0606 | | 70.0657 | | | 115.0871 | P | | | | 13 |
| 2 | 226.1192 | 209.0926 | 198.1242 | | 181.0977 | 243.1457 | Q | | | | 12 |
| 3 | 325.1870 | 308.161 | 297.1927 | | 280.1661 | 342.2141 | V | 1341.701 | 1297.712 | 1298.696 | 11 |
| 4 | 412.2196 | 395.1931 | 384.2247 | 386.2141 | 367.1981 | 429.2461 | S | 1213.643 | 1169.653 | 1170.637 | 10 |
| 5 | 513.2673 | 496.2407 | 485.2724 | 467.2618 | 468.2458 | 530.2938 | T | 1114.574 | 1070.585 | 1071.569 | 9 |
| 6 | 610.32 | 593.2935 | 582.3251 | 564.3146 | 565.2986 | 627.3466 | P | 1027.542 | 983.5526 | 984.5366 | 8 |
| 7 | 711.3677 | 694.3412 | 683.3728 | 665.3622 | 666.3463 | 728.3943 | T | 926.4947 | 882.5049 | 883.4889 | 7 |
| 8 | 824.4518 | 807.4252 | 796.4569 | 778.4463 | 779.4303 | 841.4783 | L | 829.4419 | 785.4521 | 786.4361 | 6 |
| 9 | 923.5202 | 906.4936 | 895.6253 | 877.5147 | 878.4987 | 940.5467 | V | 728.3943 | 684.4044 | 685.3885 | 5 |
| 10 | 1052.563 | 1035.536 | 1024.568 | 1006.557 | 1007.541 | 1069.589 | E | 615.3102 | 589.3309 | 572.3044 | 4 |
| 11 | 1151.631 | 1134.605 | 1123.636 | 1105.626 | 1106.61 | 1168.658 | V | 516.2418 | 490.2625 | 473.236 | 3 |
| 12 | 1238.663 | 1221.637 | 1210.668 | 1192.658 | 1193.642 | 1255.69 | S | 387.1992 | 343.2094 | 344.1934 | 2 |
| | | | | | | | R | 288.1308 | 262.1515 | 245.125 | |
| | | | | | | | | 201.0988 | 175.1195 | 158.093 | 1 |

(*)H=1.0085, PCdiff=PC$_{MS2}$−PC$_{MS3}$=227.163

MASS SPECTROMETRY SYSTEM

FIELD OF TECHNOLOGY

The present invention relates to a mass spectrometry system, which collects and analyzes data by way of mass spectrometry, and in particular to a system suited for the analysis of amino acid sequences where mass spectrum data obtained by mass spectrometry of a specimen that includes peptide mixtures, is used to estimate the amino acid sequence of individual peptides.

BACKGROUND ART

The analysis of the structure and functions of proteins has advanced rapidly in recent years as a field of post-genome research. One of the methods that has gained widespread use for the analysis (proteomic analysis) of the structures and functions of proteins uses mass spectrometry to analyze the expression and the primary structure of proteins. The so-called $MS^n$ analysis (where n is any integer equal to or greater than 2) which uses quadrupole ion traps, collision induced dissociation (CID) and the like to conduct trapping and fragmenting with regard to specific peaks is proving to be a powerful tool. In general, with the $MS^2$ (=MS/MS) analysis, an ion with a specific mass (more precisely, a mass/charge ratio (m/z)) is selected as a precursor ion from the various ions derived from the specimen to be analyzed. The precursor ion is fragmented using CID, and mass spectrometry is performed on the ions (product ions or fragment ions) that are generated by fragmentation to obtain desired information on the mass or chemical structure of the ions.

To estimate the amino acid sequence of a protein using an $MS^n$ analysis such as that described above, the protein is first digested using a suitable enzyme to obtain a peptide fragment mixture. The peptide mixture is then subjected to mass spectrometry. Since the elements that constitute the respective peptides contain stable isotopes of differing masses, peptides having the same amino acid sequence will generate a plurality of peaks of differing masses reflecting the differences in the isotope composition. Those plurality of peaks include a peak of the ion (main ion) that make up only the isotope whose natural abundance ratio is the largest and peaks of ions (isotope ions) that include other isotopes. Those peaks form a group of isotope peaks where the peaks are separated by one Da. intervals when the precursor ion is singly charged.

Next, from the mass spectrum data of a peptide mixture such as described above, one set of isotope peak groups derived from a single peptide is selected as a precursor ion. Mass spectrometry ($MS^2$ analysis) is performed on the ions that are obtained by the fragmentation of the precursor ion. If sufficiently small fragments cannot be obtained by a single fragmentation operation, the fragmentation operation is performed in multiple steps with some $MS^n$ by further selecting expected precursor ions.

Either the mass spectrum pattern of the product ions obtained as described above or the mass spectrum pattern of the precursor ion is used as a basis for performing a database search to identify the amino acid sequences with a search engine such as MASCOT, which is provided by Matrix Science Ltd., to determine the amino acid sequence, of the peptide specimen. Alternatively, various analytical software called de novo sequence can be executed on a computer to perform mathematical calculations to estimate the amino acid sequence of the peptide specimen.

Reference 1, a non-patent literature, describes one example of a known prior method for estimating an amino acid sequence using the de novo method. This method uses a mass spectrum based on an $MS^2$ analysis and a mass spectrum based on an $MS^3$ analysis which performs one more step of fragmentation. To briefly explain, the fact that ions that are observed by the $MS^2$ analysis and the $MS^3$ analysis are product ions that have the same terminal (either a C-terminal or a N-terminal) is used to estimate the partial sequences of the peptide. Partial sequences that are determined by a plurality of $MS^3$ analyses are coupled together to estimate the entire amino acid sequence of the peptide. However, the ions that are observed by both the $MS^2$ analysis and the $MS^3$ analysis reflect only some of the product ions that are formed by the fragmentation of the peptide; meaning that that information alone is insufficient for the analysis. One attempt that has been implemented to address this insufficiency is to increase the types of product ion peaks that are collected by using complementary spectrum that are obtained by inverting left and right the mass spectrum (hereinafter simply "$MS^3$ spectrum") that was obtained with the $MS^3$ analysis. The left and right inversion is performed with respect to the position (mass) of the precursor ion during the $MS^3$ analysis.

Patent Reference 1 describes increasing the product ion peaks by synthesizing a plurality of $MS^n$ spectra into a single mass spectrum. However, with this method, not only does the mass spectrum that is synthesized contain much noise but the product ions that are measured using $MS^n$ analyses whose value of n is 3 or more contain ions whose bonds are fragmented at two or more locations in the same peptide. This means that as the value of n increases, the synthesized mass spectrum pattern becomes very complicated. The result is that when the amino acid sequence of a peptide is estimated using peaks that appear in the synthesized mass spectrum, the reliability becomes poor despite the time consuming nature of the analysis.

In light of the above-described problems, the present applicant proposed a novel amino acid sequence analysis method in Patent Reference 2. To explain, what is done is to collect the peaks that are commonly present in an $MS^2$ spectrum and an $MS^3$ spectrum, the peaks that are commonly present in the $MS^2$ spectrum and the mass spectrum that is obtained after shifting the $MS^3$ spectrum by the mass of the precursor ion, and the peaks (peaks having complementarity) that are commonly present in the $MS^2$ spectrum and the mass spectrum that is obtained by folding back the $MS^3$ spectrum about the mass of the precursor ion. These many peaks are then categorized and collected as those that belong to the same terminal series, i.e., those that belong to the C-terminal series and the N-terminal series. In this way, many peaks are collected while noise peaks are eliminated. The peak list that is concentrated as b-series and y-series are then provided to an analytical software such as the de novo sequence to estimate the amino acid sequence. This improves the accuracy of the estimation of the amino acid sequence of a peptide.

However, even with this method, depending on the type of peptide that is analyzed, the reliability of the data that is provided to the analytical software decreases and the accuracy of the amino acid sequence estimation drops. There are a number of reasons for this including the fact that, even with the $MS^n$ spectrum where the number of fragmentation operation steps is increased, the ions that correspond to the peaks where mass commonality or complementarity is not found are not used and the fact that errors may be made in the classification into C-terminal or N-terminal of ions that are categorized based on mass commonality or complementarity that is found.

Patent Reference 1: U.S. Pat. No. 6,624,4087 Specification
Patent Reference 2: JP Unexamined Patent Application Publication 2007-278712A
Non-Patent Reference 1: Z. Zhang and one other, "De Novo Peptide Sequencing by Two-Dimensional Fragment Correlation Mass Spectrometry," Analytical Chemistry, Vol. 72, No. 11, Jun. 1, 2000, pp. 2337-235

DISCLOSURE OF THE INVENTION

Problems to be Solved by the Invention

The present invention has been made in light of those problems, and it is the object of the present invention to provide a mass spectrometry system that simplifies estimating amino acid sequences of proteins and peptides based on mass spectrum data and yet provide those estimations that are more accurate than before.

Means for Solving the Problems

The present invention that was made to solve the above described problems is a mass spectrometry system that uses data that is obtained by $MS^n$ analyses (where n is any integer equal to or greater than 3) to estimate an amino acid sequence, the mass spectrometry system comprising;

a) a mass spectrometry means for obtaining mass spectrum data by performing an $MS^m$ analysis (where m is any integer equal to or greater than 2) on a specimen and an $MS^{m+1}$ analysis by selecting at least one of the mass spectrum peaks that is obtained from the $MS^m$ analysis as a precursor ion;

b) a peak information collection means for extracting each of the peaks that appear in the $MS^m$ spectrum and each of the peaks that appear in an $MS^{m+1}$ spectrum obtained by the mass spectrometry means, extracting peaks that are obtained after shifting an $MS^{m+1}$ spectrum by the difference in the mass of the precursor ions when necessary, collecting mass information for ions that correspond to those peaks and preparing peak lists by classifying the mass information into those that are determined as being the same as the terminal series of the precursor ion, those that are determined as being different from the terminal series of the precursor ion and those whose terminal series of the amino acid sequence cannot be determined;

c) a peak extraction means, which uses the mass information collected by the peak information collection means, for differentiating and categorizing peaks using criteria that are based on mass complementarity of each of the $MS^m$ spectrum and $MS^{m+1}$ spectrum or the mass commonality and complementarity of each of the $MS^m$ spectrum and $MS^{m+1}$ spectrum and determines an appearance frequency of the peaks for each category;

d) an evaluation value calculation means for calculating an evaluation index value that identifies the probability of an ion that corresponds to each of the categorized peaks of being a product ion and an evaluation index value related to the terminal series of the ions, based on reliability calculated in advance for each of the categories and indicating the certainty of an ion corresponding to a peak that is included in the category of being a product ion, reliability information that includes reliability related to the terminal series of the ion, and the appearance frequency information for the peaks of each category obtained by the peak extraction means; and e) a sequence estimation means for estimating an amino acid sequence of a specimen by using mass information of the peaks categorized by the peak extraction means and the evaluation index value of each peak obtained by the evaluation value calculation means.

No particular limitations are imposed on the type or method of the "mass spectrometry means" but one typical example is a mass spectrometer equipped with a three-dimensional quadrupole mass spectrometer ion trap that can fragment a precursor ion inside the ion trap. In particular, selecting a single peak and performing an $MS^n$ analysis requires a mass spectrometer capable of selecting a precursor ion with a high resolution and performing an $MS^n$ analysis. An IT-TOF configuration that combines a three-dimensional quadrupole ion trap and a time-of-flight mass separator satisfies this condition. The ion source for the mass spectrometer can be obtained, for example, by the ionization of specimens by matrix assisted laser desorption/ionization method (MALDI).

The above "reliability calculated in advance for each of the categories that indicates the certainty of an ion corresponding to a peak that is included in the category of being a product ion and reliability information that includes reliability related to the terminal series (i.e., C-terminal or N-terminal) of the ion" are obtained in advance based on, for example, the results of the analysis of peptides whose amino acid sequence is known.

Furthermore with the mass spectrometry system according to the present invention, the peak information collection means, peak extraction means, evaluation value calculation means and sequence estimation means are executed by running predetermined programs on a general purpose computer so that the amino acid sequence is estimated by computations that are performed based on spectrum data that is provided. Here, the estimation of an amino acid sequence refers, for example, to listing a number of amino acid sequence candidates and presenting the candidates in the order of high estimation reliability or displaying the candidates together with information that indicates reliability. The above sequence estimation means may use an existing database search or a de novo sequence.

"Reliability related to the terminal series" may be, for example, the reliability that shows the possibility of an ion corresponding to the categorized peak belonging to the same terminal series as the precursor ion, the reliability of the possibility of belonging to a different terminal series or the reliability of the possibility of belonging to the C-terminal or N-terminal.

With the mass spectrometry system according to the present invention, m can be any integer equal to or greater than 2. Even though the value of m may be equal to 2, it is desirable for the value of m to be 3 or greater for increasing the accuracy of estimation of the amino acid sequence by collecting information on many peaks. When the value of m is set to be 3 or more, it is desirable to increment the value of m by one starting from 2 and executing the above processes by the respective means.

Furthermore, to collect as much peak information as possible, it is good for the mass spectrometry means to perform $MS^{m+1}$ analyses under a plurality of different fragmentation conditions on a single precursor ion and for the peak information collection means to collect the peaks that appear in the $MS^{m+1}$ spectrum that are obtained by the plurality of $MS^{m+1}$ analyses. Examples of fragmentation conditions include energy (exciting voltage, etc.) that is applied to the precursor ion and gas pressure (supply flow rate) used for collision induced dissociation. Even if the precursor ion may be identical, if the fragmentation conditions are different, the position of fragmentation of the precursor ion bonds and the like become different, creating different mass spectrum patterns.

This means the appearance of different mass peaks on the $MS^{m+1}$ spectrum and the increased number of peaks that have to be categorized using commonality or complementarity.

Also, if possible, it is good to use data that is collected by the $MS^{m+1}$ analyses using, as precursor ions, ions that are derived from the same peptide. Examples of such ions include dehydrated ions or deaminated ions that are generated by the loss of water ($H_2O$) or ammonia ($NH_3$) from the precursor ion.

It is also preferable for the peak extraction means to obtain peak information for the mass spectrum that appears when the $MS^{m+1}$ spectrum is shifted to the higher mass side just by the difference in the mass of the precursor ions for the $MS^m$ analysis and the $MS^{m+1}$ analysis and to combine the peak information so obtained and the peak information that was obtained from the original $MS^{m+1}$ spectrum to judge peak commonality or complementarity with the $MS^m$ spectrum. These shifting operations have the effect of switching the terminal series of the product ions that correspond to the peaks that appear in the mass spectrum (reversing as follows: C terminal→N terminal and N terminal→C terminal). This increases the number of peaks that are categorized using commonality or complementarity and improves the accuracy of the peak frequency information which in turn contributes to improving the reliability of the amino acid sequence estimation.

Effects of the Invention

Previously, the peak information (mass information of the ion) that is ultimately used for a database search or provided to an amino acid sequence estimation software such as a de novo sequence is assumed to be the peak of the product ion that is derived from an unknown peptide, the specimen being analyzed. Also, if information indicating whether a peak belongs to either the C-terminal or the N-terminal is available and if that information can be used for the estimation of the amino acid sequence, the terminal information was processed assuming that the terminal information was correct.

In contrast, with the mass spectrometry system according to the present invention, each peak that is extracted from the results of the mass spectrometry is provided with an evaluation index value that identifies the probability that each peak is that of a product ion and an evaluation index that identifies the reliability of the determination of the terminal type, etc. For example, the amino acid sequence can be estimated by preferentially using peaks with a high reliability of their being that of a product ion or their being determined to be of the terminal type, the accuracy of the estimation is further increased from previous times.

Furthermore, by collecting, for example, the peaks that appear in the $MS^{m+1}$ spectrum that is obtained by performing $MS^{m+1}$ analyses using different fragmentation conditions for the same precursor ion, it is possible to obtain more peaks derived from the same unknown peptide as compared to before. This allows increasing the number of peaks that are categorized based on mass commonality or difference, and this increases the reliability of the frequency of appearance of peaks for each category. This, in turn, improves the accuracy of amino acid sequence estimation.

BRIEF DESCRIPTION OF THE DRAWINGS

FIG. 3 shows one example of a peak list that was collected by an $MS^2$ analysis and an $MS^3$ analysis.

DESCRIPTION OF THE NUMERICAL REFERENCES

Figure 1:
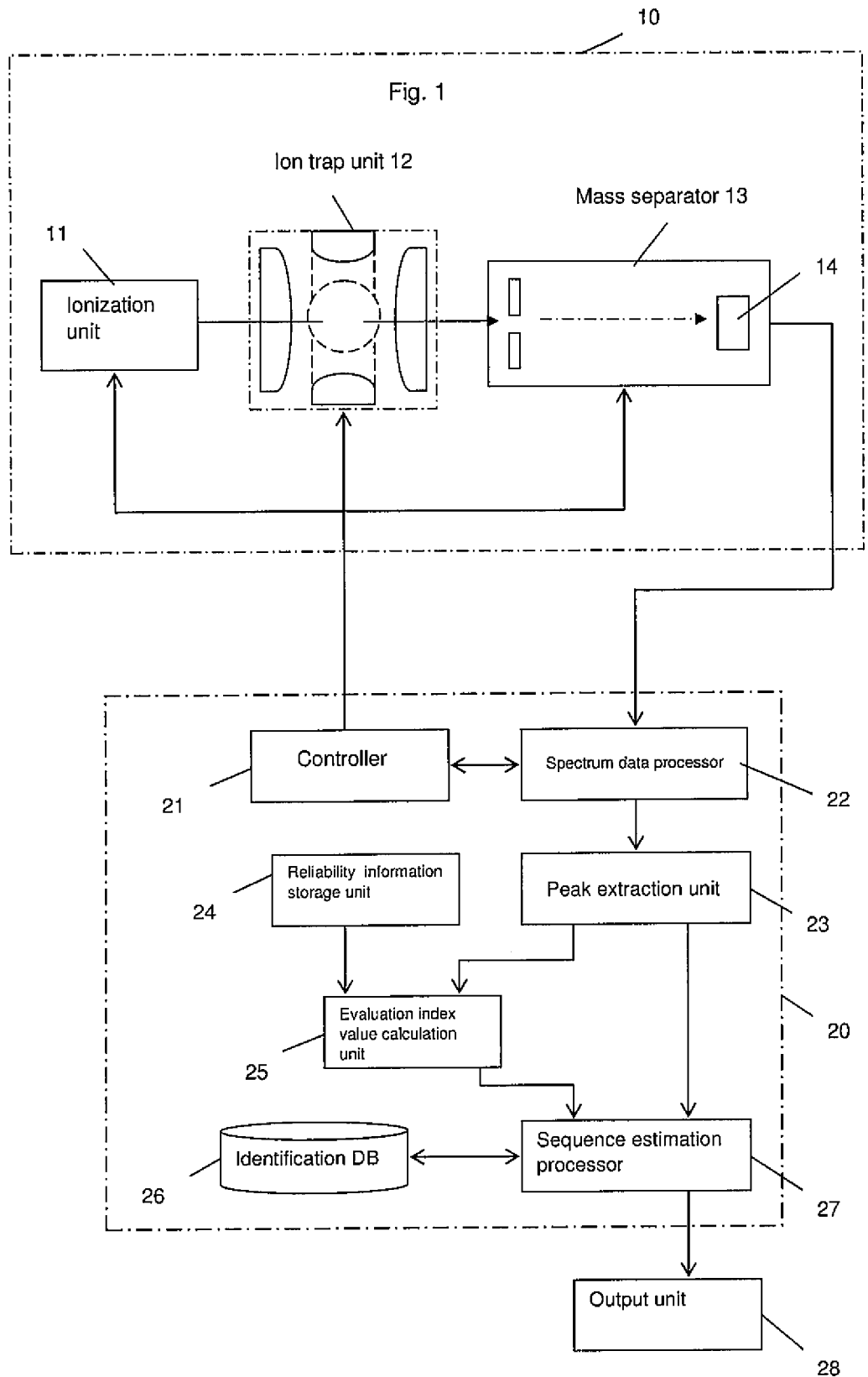
FIG. 1 shows a schematic view of one embodiment of a mass spectrometry system according to the present invention.

10. Mass spectrometry unit
11. Ionizer
12. Ion trap unit
13. Mass separator
14. Ion detector
20. Controller/processor
21. Controller
22. Spectrum data processor
23. Peak extractor
24. Reliability information storage unit
25. Evaluation index value computation unit
26. Identification database (DB)
27. Sequence estimation processor

BEST MODE FOR PRACTICING THE INVENTION

One embodiment of a mass spectrometry system according to the present invention is described next with reference to figures. The system is an amino acid sequence analysis system that estimates the amino acid sequence of the specimen, a peptide.

FIG. 1 shows a schematic view of the present embodiment of a mass spectrometry system. With the present embodiment, the system is broadly divided into a mass spectrometry unit 10 and a controller/processor 20. The mass spectrometry unit 10 includes an ionizer 11 that uses the MALDI method to ionize the specimen that includes a peptide mixture; a three-dimensional quadrupole mass spectrometer that selects an ion with a prescribed mass (more precisely, a mass/charge ratio (m/z)) as a precursor ion and generates various product ions by fragmenting the precursor ion by collision induced dissociation; a time-of-flight mass separator 13 which separates various ions emitted from the ion trap unit 12 in the direction of time depending on the ions' mass; and an ion detector 14 which sequentially detects the ions separated by their mass and outputs a detection signal that corresponds to the amount of the ions.

With this mass spectrometry unit 10, the differentiating operation and the fragmentation operation of the precursor ions in the ion trap unit 12 are alternately repeated to perform the $MS^n$ analysis (where n is any integer equal to or greater than 3). Even though there is no theoretical upper limit to the value of n for the $MS^n$ analysis, because of constraints such as the fact that the actual differentiation efficiency or the fragmentation efficiency of the precursor ion can never be 100%, the maximum value of n is generally limited to somewhere between 5 and 7.

The controller/processor 20 includes controller 21 which controls various components of the mass spectrometry unit 10 and executes the $MS^n$ analysis; spectrum data processor 22 which converts the detection signal that is obtained by the ion detector 14 to digital data and processes the digital data to create an $MS^n$ spectrum; peak extractor 23 which uses a plurality of $MS^n$ specta obtained from one specimen to perform the processes described below to differentiate and categorize peaks and furthermore determine an appearance frequency of each peak for each category; a reliability information storage unit 24 that stores in advance reliability information that is used as a reference; an evaluation index value computation unit 25 that calculates the evaluation index value for each peak based on the stored reliability information and the appearance frequency information determined by the peak extractor 23; a sequence estimation processor 27 that estimates the amino acid sequence of the specimen based on the peak information and evaluation index value for each peak; an identification database 26 that is used during the sequence estimation; and an output unit 28 that outputs the result of the estimation performed by the sequence estimation processor 27.

With the above controller/processor 20, all of the functions except for some of the functions performed by the controller 21 are realized by running a dedicated controlling/processing software that is installed on a general purpose computer.

The reliability information that is stored in the reliability information storage unit 24 is prepared in advance by using the results of the analysis of standard peptides whose amino acid sequence is known. The term "reliability information" as used in this context refers to, for number i that is assigned to each peak differentiated category further described below, the reliability, i.e., the probability $w1(i)$, that the ion corresponding to a particular peak is a product ion, the reliability, i.e., the probability $w2(i)$, that the ion corresponding to a particular peak belongs to the same terminal series as that of the precursor ion, and the reliability, i.e., the probability $w3(i)$, that the ion corresponding to a particular peak belongs to a terminal series that is different from that of the precursor ion.

Figure 2:
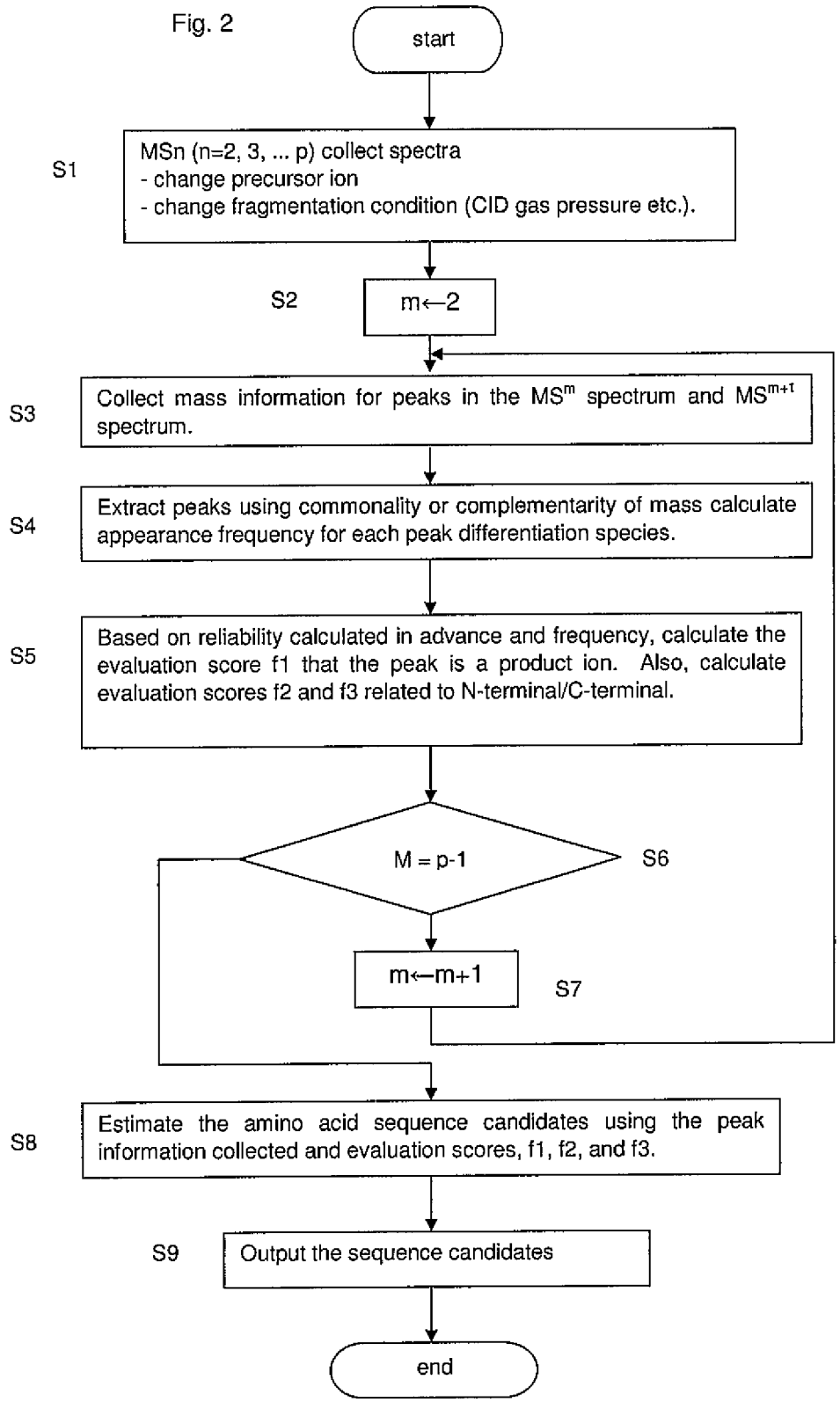
FIG. 2 shows a flowchart of the procedure used for the estimation of the amino acid sequence of a peptide in the embodiment of the mass spectrometry system.

One example of the procedure that is followed for estimating the unknown amino acid sequence of a peptide using the above mass spectrometry system is described next with reference to the flowchart shown in FIG. 2.

First, under the control of controller 21, mass spectrometry unit 10 performs a usual mass spectrometry that does not use fragmentation. A specific peak that is present in the mass spectrum (=$MS^1$ spectrum) that is obtained is selected and set as the precursor ion which is used to perform an $MS^2$ analysis, thereby producing an $MS^2$ spectrum. When doing this, it is preferable to change the fragmentation conditions such as the internal gas pressure of the ion trap unit 12 or the energy (exciting voltage) that is used with the precursor ion to obtain an $MS^2$ spectrum for each condition. Changing the fragmentation condition in this manner changes the fragmentation position of the bonds, causing the position of appearance of the peaks to change. Because the mass of peaks is different when peaks caused by some fragmentation position appear, more peaks are obtained in the $MS^2$ spectrum. Also, if peaks for dehydrated ions or deaminated ions that are present are believed to be derived from the same peptide but with water, ammonia and the like dissociated from the precursor ion, it is a good practice to perform an $MS^2$ analysis setting the ion corresponding to such peak as the precursor ion. In this way, many $MS^2$ spectra are obtained, and it is possible to dramatically increase the number of peaks that are collected later with the $MS^2$ analysis in step S2.

When the $MS^2$ spectrum is obtained, a specific peak on the mass spectrum is used as a precursor ion to perform an $MS^3$ analysis to obtain an $MS^3$ spectrum. Just as with the $MS^2$ analysis, it is good to change the fragmentation conditions or to use as the precursor ion the desorption ion of water or ammonium from the precursor ion to obtain a plurality of types of $MS^3$ spectra. Furthermore, a specific peak of the $MS^3$ spectrum is set as the precursor ion as necessary to perform an $MS^4$ analysis to obtain an $MS^4$ spectrum. In this way, the $MS^n$ analysis that is performed is accompanied by a predetermined number of steps, p, of fragmentation operations (step S1), For example, an $MS^1$ analysis, an $MS^2$ analysis, an $MS^3$ analysis and an $MS^4$ analysis are performed assuming p=4.

Next, the variable m is initialized to 2 (step S2). The mass information of the peaks obtained from the $MS^m$ spectrum and the $MS^{m+1}$ spectrum is collected to create a peak list (step S3). It is good to calculate the mass spectrum where the $MS^{m+1}$ spectrum is shifted to the high mass side just by the difference in the mass of the precursor ions for the $MS^m$ analysis and the $MS^{m+1}$ analysis and to collect the mass information for the peak that appears in the mass spectrum. When the mass information for the peaks is collected, three peak lists are created by determining if each peak has the same terminal series as the precursor ion, a different terminal series as the precursor ion, or the terminal series is unknown (indeterminable). Specifically, if the precursor ion of the $MS^3$ analysis is the y ion (C-terminal fragment ion), the peak that appears in the $MS^3$ mass spectrum is that of an ion of the same series (i.e., C-terminal) as the precursor ion. Also, a shifting process such as the above switches the terminal series as follows: C-terminal→N-terminal and N-terminal→C-terminal, Next, using the mass information of the peaks that was collected as described, peaks that are usable (or believed to be usable) are extracted. These peaks are then categorized under each different species. For each species, an appearance frequency (frequency count) of the peaks is analyzed (step S4). As an example, the explanation below assumes measuring a peptide whose amino acid sequence is [K V P Q V S T P T L V E V S R] and is based on a theoretical product ion that is obtained with an $MS^2$ analysis assuming a mass, $PCMS^2$, of the precursor ion to be 1639.938 and with an $MS^3$ analysis assuming a mass, $PCMS^3$, of the precursor ion to be 1412.775. FIG. 3 shows the mass information of this theoretical product ion. Here, the term "b/y pair" is used to refer to ones that satisfy complementarity (meaning that the sum of the peak masses of the two is equal to the mass of the precursor ion).

The possibility is high that a b/y pair (written as by0), which is a combination of the y ion (C terminal series product ion) and the b ion (N terminal series product ion), which are extracted from the $MS^2$ spectrum, or a b/y pair (written as by00), which is a combination of the y ion and the b ion, which are extracted from the $MS^3$ spectrum, are product ions. For this reason, by0 and by00 are used as peak differentiation species. However, differentiating these ions as N-terminal series or C-terminal series cannot be made. In the example shown in FIG. 3, the peaks with the following mass are extracted as by0 and by00.

by0: 1465.827+175.1195=PCMS2+H
by00: 1238.663+175.1195=PCMS3+H

With either ions, it is unclear whether it is an ion of the same terminal series or an ion of a different series as that of the precursor ion.

The peak (common peak and also written as "com1") that appears commonly in the $MS^2$ spectrum and the $MS^3$ spectrum (i.e., the peak with the same mass) is a fragment series having the same terminal series as the precursor ion. When the position of each peak that appears in the $MS^3$ spectrum is shifted to a high mass side by the difference (PC diff) in mass between the $PCMS^2$ mass of the precursor ion for the $MS^2$ spectrum and the $PCMS^3$ mass of the precursor ion for the $MS^3$ spectrum, it is determined that those peaks and the peaks that commonly appear in the $MS^2$ spectrum (common peak written as "com2") are a fragment series with a terminal series that is different from that of the precursor ion. Both com1 and com2 are used as peak differentiation species. With the example shown in FIG. 3, the peaks with the following mass are extracted as com1 and com2.

com1: 262.1515=262.1515
com2: 1279.726=(1052.563+PC diff)

com1 is an ion with the same terminal series as the precursor ion for both $MS^2$ and $MS^3$. com2 is an ion with a different terminal series from that of the precursor ion for both $MS^2$ and $MS^3$.

A b/y pair that is equivalent to the PCMS2 mass or the PCMS3 mass of the precursor ion is determined respectively from the $MS^2$ spectrum and the $MS^3$ spectrum. The b/y pair that is determined from the $MS^2$ spectrum is written as "by2." The b/y pair that is determined from the $MS^3$ spectrum is written as "by3." They can differentiate whether the terminal is the same or different from that of the precursor ion. Among by2 and by3, those that have the same or different terminal as that of the precursor ion are each divided and classified as peak differentiation species. Here, the nomenclature "by2+" is used to identify a by2 that has the same terminal as the precursor ion for $MS^2$ but a different terminal as that of the precursor ion for $MS^3$. The nomenclature "by2−" is used to identify a b/y2 that has a different terminal from that of the precursor ion for $MS^2$ but the same terminal as the precursor ion for $MS^3$. The nomenclature "by3+" is used to identify b/y3 that has the same terminal as the precursor ion for $MS^2$ but a different terminal as that of the precursor ion for $MS^3$. The nomenclature "by3−" is used to identify by3 that has the different terminal as that of the precursor ion for $MS^2$ but the same terminal as that of the precursor ion for $MS^3$.

With the example shown in FIG. 3, the peaks with the following mass are selected as by2+, by2−, by3+ and by3−.

by2+; 589.3309+(824.4518+PC diff)=PCMS2+H
by2−: 1150.684+490.2625=PCMS2+
by3+: (702.415−PC diff)+(711.3677+PC diff)=PCMS3+H
by3−: (1051.605−PC diff)+589.3309=PCMS3+H If, as described above, the same precursor ion is used while changing the fragmentation conditions to obtain a plurality of $MS^n$ spectra, even though common peaks and b/y pairs can be extracted as described above, differentiating between N-terminal series and C-terminal series cannot be made. Furthermore, even though it is possible to extract common peaks and b/y pairs between an $MS^n$ spectrum that was obtained using a neutral loss peak as a precursor ion and an $MS^n$ spectrum that was obtained using a peak with no loss as a precursor ion, differentiate between N-terminal and C-terminal cannot be made. Even though this is not described in FIG. 3, differentiating peak species is possible.

The many peaks that appear in the mass spectrum that was obtained in step S2 as described above can be categorized into a plurality of peak differentiation species. The number of peaks that are classified into each peak differentiation species is counted to determine the appearance frequency. The peaks that are not extracted are deemed to be noise peaks and are excluded from further processing.

The peak differentiation species such as described above are assigned a serial number that starts from 1. Eight species of peak differentiation species, by0, by00, com1, com2, by2+, by2−, by3+ and by3−, are expressly shown in the example described above. In fact, however, peak is differentiated into 16 species and serial numbers are assigned. And, for each peak differentiation species number i (i=0, 1, ..., 16), the reliability $w1(i)$ that shows the probability of being a product ion and frequency $n1(i)$ determined in step S3 are multiplied and summed to arrive at evaluation score value f1 which is used for evaluating whether or not the extracted peak is a product ion. To explain, $fk=\Sigma wk(i) \cdot nk(i)$, where k=1 for the sum of i=1 through 16.

Similarly, based on reliability $w2(i)$ that shows the probability that an extracted peak has the same terminal as the precursor ion and frequency $n2(i)$ with which an actual peak is differentiated as having the same terminal as the precursor ion, evaluation score f2 that a differentiated peak has the same terminal as the precursor ion is determined. Furthermore, based on reliability $w3(i)$ that shows the probability that an extracted peak has a different terminal from the precursor ion and frequency $n3(i)$ with which an actual peak is differentiated as having a different terminal as the precursor ion, evaluation score f3 that a differentiated peak has a different terminal as the precursor ion is determined (step S5).

Thereafter, the value of m is incremented by 1, and if the value of (m+1) has not reached a predetermined maximum value (steps S6, S7), control returns to step S2, and the processes in steps S2 through S4 are repeated. To explain, if m=3, the mass information for the peaks that are obtained from the $MS^3$ spectrum and the $MS^4$ spectrum are collected. Extraction of peaks, categorization and calculation of frequency are performed to determine the evaluation score. These processes are repeated until the value of (m+1) reaches a predetermined maximum value.

Using the mass information for the peaks that are extracted as described above, i.e., by using the peak list, a database search is conducted to estimate a number of peptide sequence candidates (step S8). Alternatively, a de novo sequence can be used to estimate a number of candidates. Evaluation scores f1, f2 and f3 determined in step S4 are used when outputting these sequence candidates from the output unit 28. For example, those whose evaluation score f1 of the peak that was used for identifying/estimating the peptide sequence candidate is high or those whose evaluation score f2 and f3 related to the terminal series match the assumption that is made for the identification/estimation are selected as priority candidates. For this reason, it is possible to calculate for each sequence candidate the reliability score for sequence estimation that references evaluation scores f1 through f3, or preferentially display sequences with high reliability scores, or display sequences and reliability scores at the same time.

It is also possible to use the evaluation scores for the peaks when estimating sequence candidates using database search or a de novo sequence. One simplest method is, for example, not to use a peak for sequence estimation when the evaluation score for the peak is less than a certain standard value. A method such as this is particularly effective when the number of peaks that appear in a mass spectrum is numerous.

In the above described way, the present embodiment of the mass spectrometry system allows candidates of amino acid sequences of peptide mixtures that are being analyzed to be displayed with a high reliability.

Needless to say, the above described embodiment is only one example of a way in which the present invention can be practiced, and various modifications, additions and the like can be made to the present invention without deviating from the concept of the invention and the scope of the claims of this application.

What is claimed is:
1. A mass spectrometry system that uses data obtained by $MS^n$ analyses where n is any integer equal to or greater than 3, to estimate an amino acid sequence, the mass spectrometry system comprising:
 a) a mass spectrometry means for obtaining mass spectrum data by performing an $MS^m$ analysis where m is any integer equal to or greater than 2, on a specimen and an

$MS^{m+1}$ analysis by selecting at least one of the mass spectrum peaks that is obtained from the $MS^m$ analysis as a precursor ion;

b) a peak information collection means for extracting each of the peaks that appear in an $MS^m$ spectrum and each of the peaks that appear in an $MS^{m+1}$ spectrum obtained by the mass spectrometry means, extracting peaks that are obtained after shifting the $MS^{m+1}$ spectrum by the difference in the mass of the precursor ions when necessary, collecting mass information for ions that correspond to the peaks, and preparing peak lists by classifying the mass information into those that are determined as being the same as the terminal series of the precursor ion, those that are determined as being different from the terminal series of the precursor ion and those whose terminal series of the amino acid sequence cannot be determined;

c) a peak extraction means using the mass information collected by the peak information collection means, for differentiating and categorizing peaks using criteria that are based on mass complementarity of each of the $MS^m$ spectrum and the $MS^{m+1}$ spectrum or the mass commonality and complementarity of each of the $MS^m$ spectrum and the $MS^{m+1}$ spectrum and determining an appearance frequency of the peaks for each category;

d) an evaluation value calculation means for calculating an evaluation index value that identifies the probability of an ion that corresponds to each of the categorized peaks of being a product ion and an evaluation index value related to the terminal series of the ions, by using reliability calculated in advance for each of the categories that indicates the certainty of an ion corresponding to a peak that is included in the category of being a production, reliability information that includes the reliability related to the terminal series of the ion and the appearance frequency information for the peaks of each category obtained by the peak extraction means,; and e) a sequence estimation means for estimating the amino acid sequence of the specimen by using the mass information of the peaks differentiated by the peak extraction means and the evaluation index value of each peak obtained by the evaluation value calculation means.

2. The mass spectrometry system according to claim 1 wherein the value of m is 3 or more and the processes performed by the respective means are executed in the sequence of m=2, 3, . . . .

3. The mass spectrometry system according to claim 1 wherein the peak information collection means collects peaks that appear in the $MS^{m+1}$ spectrum that are obtained by performing the $MS^{m+1}$ analysis using a plurality of different fragmentation conditions on one certain precursor ion.

4. The mass spectrometry system according to claim 1 wherein the peak extraction means obtains information on peaks that appear in the mass spectrum that is obtained by shifting the $MS^{m+1}$ spectrum to the high mass side by the difference in the mass of the precursor ions for the $MS^m$ analysis and the $MS^{m+1}$ analysis and combining this information with the information on peaks that are obtained from the original $MS^{m+1}$ spectrum to determine the commonality or complementarity of peaks with the $MS^m$ spectrum.

* * * * *